United States Patent
Wildemeersch

(10) Patent No.: US 8,430,101 B2
(45) Date of Patent: Apr. 30, 2013

(54) PLASTIC FRAME FOR AN INTRAUTERINE DEVICE

(75) Inventor: Dirk Wildemeersch, Ghent (BE)

(73) Assignee: PAT&Co bvba, Lichtervelde (BE)

( * ) Notice: Subject to any disclaimer, the term of this patent is extended or adjusted under 35 U.S.C. 154(b) by 44 days.

(21) Appl. No.: 13/140,978

(22) PCT Filed: Dec. 21, 2009

(86) PCT No.: PCT/EP2009/067704
§ 371 (c)(1), (2), (4) Date: Jun. 20, 2011

(87) PCT Pub. No.: WO2010/070150
PCT Pub. Date: Jun. 24, 2010

(65) Prior Publication Data
US 2011/0253148 A1 Oct. 20, 2011

(30) Foreign Application Priority Data
Dec. 19, 2008 (EP) .................................. 08106019

(51) Int. Cl.
*A61F 6/06* (2006.01)
(52) U.S. Cl.
USPC ......................................................... 128/833
(58) Field of Classification Search ........... 128/830–841
See application file for complete search history.

(56) References Cited

U.S. PATENT DOCUMENTS

| 3,952,734 A | 4/1976 | Van |
| RE30,312 E * | 6/1980 | Kessel ........................... 128/839 |
| 5,494,047 A * | 2/1996 | Van Os ........................... 128/832 |
| 6,030,375 A * | 2/2000 | Anderson et al. .......... 604/890.1 |
| 7,080,647 B2 | 7/2006 | Wildemeersch |
| 2004/0261799 A1* | 12/2004 | Mock ............................ 128/833 |

FOREIGN PATENT DOCUMENTS
WO 2007075086 7/2007

OTHER PUBLICATIONS
International search report dated Apr. 16, 2010 in corresponding PCT/EP2009/067704.

* cited by examiner

Primary Examiner — Patricia Bianco
Assistant Examiner — Tarla Patel
(74) Attorney, Agent, or Firm — Young & Thompson

(57) ABSTRACT

An intrauterine device (IUD) for delivering bioactive substances in the uterine cavity includes a plastic frame affixed to a drug delivery compartment. The frame retains the IUD in the uterine cavity and prevents displacement and expulsion. The frame is shaped like the letter "omega" having two resilient arms which possess latero-lateral memory. The extremities of the arms are provided by a short side-arm which forms an angle with the rest of the arm. These prominent plastic parts facilitate the upward rotation of the arms during removal of the intrauterine device. The drug delivery compartment has an element at its upper extremity to determine the exact location of the IUD in the uterine cavity by ultrasound. The drug delivery compartment contains one or more drugs which are gradually released in the uterine cavity over extended periods of time.

15 Claims, 2 Drawing Sheets

PLASTIC FRAME FOR AN INTRAUTERINE DEVICE

FIELD AND BACKGROUND OF THE INVENTION

Intrauterine drug delivery is becoming increasingly important in gynecological practice. Intrauterine drug delivery can be used for contraception and treatment of various gynecological conditions. However, with existing intrauterine systems, delivering hormones in the uterus, there are several drawbacks which can be improved such as the ease of insertion in the uterine cavity, adaptation of the plastic frame to different sizes and shapes of uterine cavities to minimize side effects, retention of the IUD in the uterus, retrieval of the intrauterine foreign body from the uterus and visibility of the body on ultrasound examination.

The plastic frame of intrauterine devices (IUD) often creates dimensional incompatibility with the uterine cavity which could give rise to complaints such as abnormal uterine bleeding and cramping pain. Incompatibility also leads to displacement and expulsion of the IUD.

In an attempt to improve compatibility with uterine cavities of different sizes and shapes, and avoid expulsion and translocation, the "Multiload®" IUD (Organon) was created wherein the arms are approximately in the shape of the letter "omega" (see U.S. Pat. No. 3,952,734) and comprise lateral extensions. However, although the curved arms can adapt to the width of various uterine cavities, the arms are not enough resilient and, therefore, downward displacement of the IUD is not prevented by the design characteristics of the IUD. The arms of the Multiload® IUD also form an integral part of the plastic frame and cannot rotate during retrieval of the device from the uterine cavity. Removal of the Multiload IUD® requested by the woman is therefore sometimes difficult, painful and could also damage the uterus. One or both arms could also break off during removal of the device which can lead to complications.

Ultrasound examination has become routine in gynecological practice. The proper performance of the IUD is related to the proper position of the IUD in the uterine cavity. The assessment of the proper location of an intrauterine system in the uterine cavity by ultrasound which does not contain a metal such as copper is sometimes difficult, especially if there are uterine abnormalities.

To enhance the visibility of the drug-releasing IUD on ultrasound, the development of simple means will facilitate the location of the device in the uterine cavity. This can be accomplished by increasing the density of a part of the drug delivery compartment. The best way to assess the proper location of the IUD in the uterine cavity is by measuring the distance between the outer and upper surface of the uterus and the upper extremity of the drug delivery compartment. The more denser part of the drug delivery rod should therefore be selected to make it denser and more visible on ultrasound.

Another important aspect is the assembly of the plastic frame with the drug delivery compartment. The assembly of a plastic component which has multiple curves, with the rod-shaped drug delivery compartment is not evident. First, from a manufacturing point of view it is important that the plastic part can easily be assembled with the drug delivery rod. Therefore, the plastic frame should be resilient to allow straightening of the curves. The frame should not be provided with hooks or prongs such as those provided in the Multiload® IUD which would prevent the assembly with the drug delivery compartment. Secondly, it should be so constructed that its acts as a proper retaining member and, simultaneously, allows adaptation to the great differences in width of uterine cavities and thirdly, the assembly should allow easy upward rotation of the plastic frame during caudal traction on the IUD to allow easy removal of the IUD from the uterine cavity.

The aim of the present invention is to optimize intrauterine drug delivery to facilitate insertion, enhance acceptability and tolerance, improve retention, facilitate or even make removal possible and enhance visibility by ultrasound to allow assessment of the proper positioning of the IUD in the uterine cavity. To this end, the present invention concerns the design of a new platform for the delivery of drug(s) in the uterus for contraceptive and treatment purposes, easy to insert and remarkable well tolerated by parous, nulligravid/nulliparous women and women in the postmenopausal phase which have uteri which markedly differ in size and shape and are usually very small.

The present invention constitutes also an improvement of the intrauterine device disclosed in WO 03/068117 or U.S. Pat. No. 7,080,647 B2, these latter documents being incorporated herein by reference.

SUMMARY OF THE INVENTION

According to the present invention, a drug delivery platform is provided of which the plastic frame is approximately omega-shaped or partly oval-shaped when placed in the uterine cavity, the arms of which are resilient in latero-lateral direction and which allow adaptation and retention in uterine cavities of different size and shape and of which the plastic frame can easily be assembled with a straight drug delivery rod. An additional aim of the present invention is to provide a plastic frame which is provided with a means to allow easy upward rotation of the arms during removal of the IUD.

A further aim of the invention is to enhance the visibility of the IUD on ultrasound.

These goals are reached, according to the present invention, by providing an IUD which consists mainly of two parts:—the stem of the IUD which is the drug delivery compartment, or rod—and the plastic frame or retaining member of the IUD. The drug delivery compartment contains the active pharmaceutical ingredient (API), which can be a hormone, or any other bioactive or chemical substance, and which functions as vertical stem of the IUD, and is lying in the longitudinal axis of the uterine cavity. The loaded drug delivery rod consists preferably of a polymer which is sufficiently resilient to prevent damage of the uterine wall during use of the IUD and adapts to the curvature of the uterine cavity. The plastic frame, according to the invention comprises two curved arms, approximately "omega" shaped, when located in the uterus and consists of a material which is sufficiently resilient to adapt to uterine cavities which differs in size and shape and which exerts latero-lateral pressure on the uterine wall to enhance retention of the IUD in the uterine cavity. Material of the plastic frame part may be any biocompatible resilient plastic, for example polyethylene. The plastic frame, according to the invention can be straightened in order to allow its insertion and fixation through a hole made in the upper part of the drug delivery rod. The plastic frame lies in the upper part of the uterine cavity and is held in position by the stem of the IUD, being the drug delivery component.

According to another characteristic of the invention, the arms of the plastic frame can adapt to cavities of every size and shape by approximation and exert lateral pressure on the side walls of the uterine cavity.

According to an additional characteristic of the invention, the plastic frame is provided with a narrow part in the middle which, at assembly with the drug delivery rod, is the part that is connected with the upper part of the drug delivery compartment. This stabilizes the assembly and reduces the frictional force. It facilitates the rotation of the plastic part within the hole of the compartment when.

According to yet another characteristic of the invention, the tips of the arms of the omega-shaped plastic frame are curved forming an angle of at least 45° with the main body of the frame. Preferably the angle is above 80°, still preferably 90°.

According to yet another characteristic of the invention, the plastic frame is able to rotate in anterior or posterior direction, along an axis formed by the connecting hole in the upper part of the drug delivery rod, when traction is exerted on its lower end to remove the IUD from the uterine cavity.

According to another characteristic of the invention, the drug delivery compartment, at its upper and lower extremity, is denser in composition than the rest of the drug delivery rod.

According to another characteristic of the invention, the ends of the drug delivery rod are rounded off or dome shaped to facilitate insertion of the IUD in the uterine cavity.

According to yet another characteristic of the invention, the drug delivery compartment is between 2 and 4 cm long.

According to an additional characteristic of the invention, a small hole is provided in the lower part of the drug delivery compartment to allow the tying of a removal thread.

According to another aspect of the invention during the manufacturing phase, the plastic frame is introduced by one of its ends in the hole provided in the upper part of the compartment element. This may be made by force. The flexibility and the diameter of the linear plastic frame should therefore be appropriate in this regard. In particular, the diameter along the plastic arms should be adapted to permit the sliding inside the hole. The diameter may vary from the end up to the mid-section of the omega-shaped plastic member.

BRIEF DESCRIPTION OF THE DRAWINGS

These and other characteristics of the invention will be more readily understood when referring to the description as well as the accompanying drawings which represent, merely by way of examples, several embodiments of the invention, and in which.

DETAILED DESCRIPTION

Figure 1A:
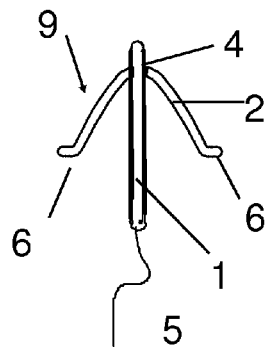
FIGS. 1a and 1b represent in a very schematic way a preferred embodiment of an IUD according to the invention, showing the two parts of the IUD: the curved shaped part 2 and the straight drug delivery rod 1.
Figure 1B:
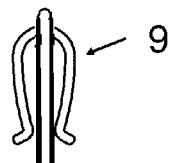

Referring now particularly to FIGS. 1a and 1b, the IUD according to a embodiment of the invention is illustrated respectively in the relaxed state and in the folded state. The IUD consists essentially of a plastic frame 2 made in a material which is resilient, and a drug delivery compartment 1 also made in a material which is resilient and flexible. The midsection of the plastic frame is connected with the drug delivery rod 1 through a hole 4 in the its upper part forming an assembly which is easily inserted in the uterus with a hollow tube (e) when the drug delivery rod is inserted in the tube. Also illustrated are small ends 6 of the arms of the plastic frame, extending outwardly. These elements due to the resilience of the arms are in contact of the wall of the uterus.

Figure 2:
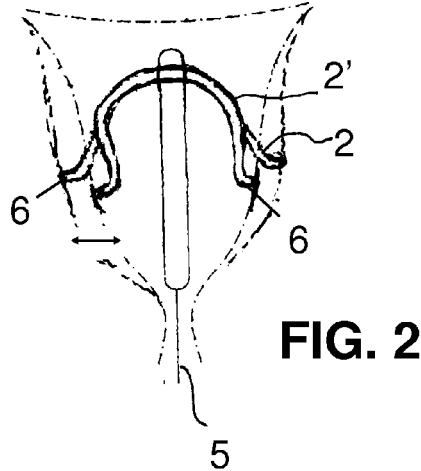
FIG. 2 is a schematic cross sectional view of the uterus with a preferred embodiment of an IUD according to the invention, showing the possibility of adaptation of the plastic frame according to different widths of uterine cavities.

According to the representation in FIG. 2, the plastic frame 2 allows approximation of the arms of the frame to adapt to different widths of uterine cavities. If the uterus is wider, the plastic frame 2 extends laterally to make contact with the uterine wall on both sides to maximize retention of the IUD in the uterine cavity. During insertion of the IUD in the uterine cavity, the arms 2a and 2b fold and the memory of plastic will adjust the arms to the width of the uterine cavity.

Figure 3:
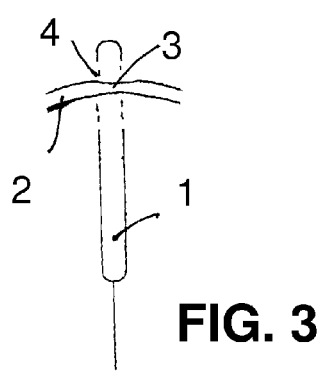
FIG. 3 is another schematic cross sectional view through the connection of the two elements of the IUD showing the narrow part 3 of the plastic frame when assembled in the hole made in the upper part of the drug delivery rod and along which the plastic part can rotate.

According to FIG. 3, the plastic frame 2 has a narrow part 3 in its middle section for the fixation of the frame in hole 4 of the drug delivery rod 1 which prevents frictionally easy dislodgement of the two parts.

Figure 4:
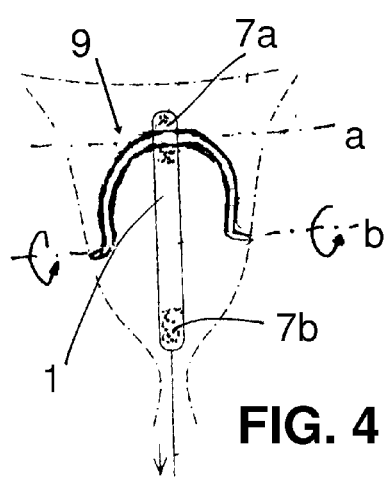
FIG. 4 represents another schematic cross sectional view of the uterus with a preferred embodiment of an IUD according to the invention showing rotation of the plastic frame, during removal of the IUD from the uterine cavity, around an axis through the narrow part of the plastic frame of the IUD. The presence of small plastic ends of the arms which form an angle with the body of the plastic frame allows the rotation to take place.
Figure 5:
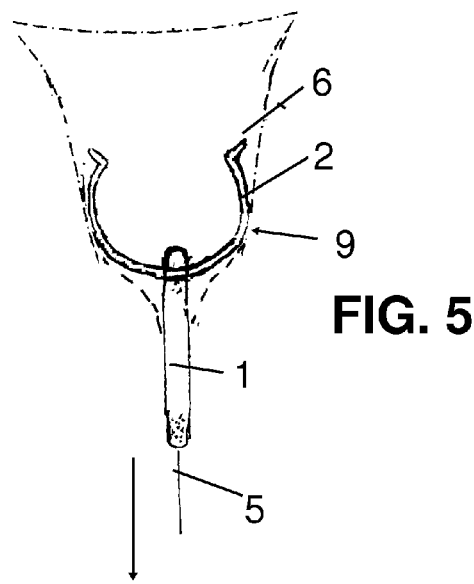
FIG. 5 represents another schematic cross sectional view of the upper and lower denser ends of the drug delivery rod and the rounding of the tips.

According to FIG. 4, the plastic frame 2 "pivots" around its axis "a" which is formed by the connection of the narrow part 3 and the hole 4 in the drug delivery rod 1 when caudal traction is exerted on the tail or thread 5 which is connected to the lower end of the drug delivery compartment 1. According to the invention the small ends 6 facilitate rotation, forming an axis of rotation "b" of the device at least during the initial withdrawing movement as shown in FIG. 5.

The denser tips (7a and 7b) of the drug delivery rod increase the visibility of the IUD by ultrasound examination.

Figure 6:
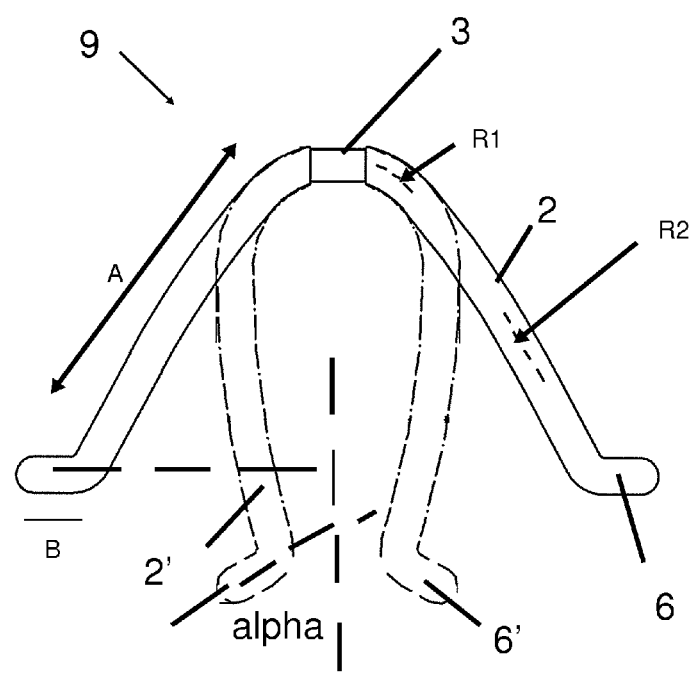
FIG. 6 is a view of the plastic frame according to the invention in both relaxed configuration and folded configuration.

FIG. 6 is an enlarged view of the plastic frame according to the invention in both relaxed configuration and folded configuration. The frame has an essentially semi-oval shape, with however arms having a near straight section A.

Typically the radius of the upper curvature is 4-5 mm and of the near straight section 35-45 mm. Diameter of the arms is around 1.6 mm and diameter at the medial straight, which is around 2.4 mm long, is narrower by 2 mm. The elements 6 are 3 mm long and their ends are rounded.

The invention has been described and illustrated merely by way of examples which are in no way restrictive. Numerous changes in its conception may be made without departing from the scope of the invention as defined in the attached claims.

The invention claimed is:
1. An intrauterine device (IUD) comprising:
a substantially straight compartment configured to deliver at least one bioactive substance within a uterus, the straight compartment having a transversal hole provided in an upper extremity thereof; and
a curved plastic frame configured to be sufficiently resilient and extendable to adapt to various sizes and shapes of a plurality of uteruses, the curved plastic frame including ends, each of the ends comprising a protruding element extending outwardly therefrom, the curved plastic frame being securely fixed to the straight compartment through the transversal hole provided in the upper extremity of the straight compartment, wherein the frame is configured to pivot within the hole when traction is exerted on a lower end of the straight compartment to allow removal of the IUD from the uterus to which the bioactive substance is delivered.

2. The IUD according to claim 1, wherein the protruding elements are elongated elements whose directions form an angle alpha of 45° to 90° with the straight compartment.

3. The IUD according to claim 1, wherein the protruding elements are straight extending elements.

4. The IUD according to claim 1, wherein the protruding elements are essentially perpendicular to said straight compartment.

5. The IUD according to claim 1, wherein the median part of the plastic frame comprises a section of narrower diameter than remaining parts of the plastic frame.

6. The IUD according to claim 1, wherein the median part of the plastic frame includes a straight section.

7. The IUD according to claim 1, wherein the protruding elements extending outwardly define an axis of rotation of the curved plastic frame while the curved plastic frame is pivoting in the hole of the straight compartment when traction is exerted downwardly for removal.

8. The IUD according to claim 1, wherein the substantially straight compartment is a drug delivery rod having a dome-shaped tip for facilitating insertion of the IUD in the uterus.

9. The IUD according to claim 8, wherein at least one end of the drug delivery rod includes a denser material than a middle section of the drug delivery rod.

10. The IUD according to claim 1, wherein the straight compartment has a diameter between 2 and 3.5 mm.

11. The IUD according to claim 1, wherein the protruding elements outwardly extending are 2 to 5 mm long.

12. The IUD according to claim 1, wherein the straight compartment is 25 to 40 mm long.

13. The IUD according to claim 1, wherein the device is a contraceptive device.

14. The IUD according to claim 1, wherein the device is configured for gynecological treatment.

15. The IUD according to claim 1, wherein the curved plastic frame includes a pair of arms, each arm including a main section extending from a central axis of the curved plastic frame and one of the ends of the curved plastic frame, and each of the protruding elements extends outwardly from the main section of each of the arms at the ends of the plastic frame.

* * * * *

UNITED STATES PATENT AND TRADEMARK OFFICE
CERTIFICATE OF CORRECTION

PATENT NO. : 8,430,101 B2 Page 1 of 1
APPLICATION NO. : 13/140978
DATED : April 30, 2013
INVENTOR(S) : Dirk Wildemeersch It is certified that error appears in the above-identified patent and that said Letters Patent is hereby corrected as shown below:

On the Title Page:

The first or sole Notice should read --

Subject to any disclaimer, the term of this patent is extended or adjusted under 35 U.S.C. 154(b) by 46 days.

Signed and Sealed this
Eighth Day of September, 2015

Michelle K. Lee
*Director of the United States Patent and Trademark Office*